United States Patent
Kim et al.

(10) Patent No.: US 9,504,703 B2
(45) Date of Patent: Nov. 29, 2016

(54) EQUOL CONCENTRATION INCREASING AGENT CONTAINING PSICOSE AS ACTIVE INGREDIENT

(71) Applicant: CJ CHEILJEDANG CORPORATION, Seoul (KR)

(72) Inventors: Taek Beom Kim, Seoul (KR); Seong Bo Kim, Seoul (KR); Min Hae Kim, Incheon (KR); Sung Jae Yang, Gwangmyeong-si (KR); Jae Hong Han, Gwacheon-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 111 days.

(21) Appl. No.: 14/361,528

(22) PCT Filed: Oct. 15, 2012

(86) PCT No.: PCT/KR2012/008398
§ 371 (c)(1),
(2) Date: May 29, 2014

(87) PCT Pub. No.: WO2013/081294
PCT Pub. Date: Jun. 6, 2013

(65) Prior Publication Data
US 2014/0329286 A1 Nov. 6, 2014

(30) Foreign Application Priority Data
Nov. 30, 2011 (KR) ........................ 10-2011-0126552

(51) Int. Cl.
| | | |
|---|---|---|
| *C12P 17/06* | (2006.01) | |
| *A61K 31/7004* | (2006.01) | |
| *C12N 1/20* | (2006.01) | |
| *C12N 1/38* | (2006.01) | |
| *A61K 9/00* | (2006.01) | |
| *A61K 9/20* | (2006.01) | |
| *A61K 31/352* | (2006.01) | |
| *A61K 35/74* | (2015.01) | |
| *A23L 2/52* | (2006.01) | |
| *A23L 2/60* | (2006.01) | |

(52) U.S. Cl.
CPC ............. *A61K 31/7004* (2013.01); *A23L 2/52* (2013.01); *A23L 2/60* (2013.01); *A23L 33/10* (2016.08); *A61K 9/0095* (2013.01); *A61K 9/2054* (2013.01); *A61K 31/352* (2013.01); *A61K 35/74* (2013.01); *C12N 1/20* (2013.01); *C12N 1/38* (2013.01); *C12P 17/06* (2013.01); *A23V 2002/00* (2013.01)

(58) Field of Classification Search
None
See application file for complete search history.

(56) References Cited

U.S. PATENT DOCUMENTS

| | | |
|---|---|---|
| 9,080,197 B2 | 7/2015 | Tsuji et al. |
| 2009/0069269 A1 | 3/2009 | Tamura et al. |

FOREIGN PATENT DOCUMENTS

| | | |
|---|---|---|
| EP | 1 757 297 A1 | 2/2007 |
| EP | 1 944 021 A1 | 7/2008 |
| KR | 10-2006-0028436 A | 3/2006 |
| KR | 10-2008-0072635 A | 8/2008 |
| KR | 10-2009-0077072 A | 7/2009 |
| WO | WO 2007/052740 A1 | 5/2007 |

OTHER PUBLICATIONS

Matsuo et al., Asia Pacific J Clin Nutr, 2001, vol. 10, No. 3, p. 233-237.*
Lida et al., Metabolism Clinical and Experimental, 2010, vol. 59, p. 206-214, Epub Sep. 17, 2009.*
Minamida et al., Journal of Bioscience and Bioengineering, 2006, vol. 102, No. 3, 247-250.*
Yu et al., FEMS Microbiol. Lett., 2008, vol. 282, No. 1, p. 73-80.*
Nagata, "Composition useful as food additive and health food for treating diabetes and obesity, contains D-psicose and/or its derivatives which suppresses rapid increase of blood glucose level after ingesting with saccharides," WPI/Thomson 2005(57), Aug. 11, 2008, 2 pages. (Abstract Only).

* cited by examiner

*Primary Examiner* — Kade Ariani
(74) *Attorney, Agent, or Firm* — Seed IP Law Group LLP

(57) ABSTRACT

The present invention relates to a processed food composition containing, as an active ingredient, psicose, which is a saccharide having the function of stimulating a daidzein conversion into equol by an intestinal microorganism in the human body.

2 Claims, 3 Drawing Sheets

<solvent> toluene : acetone = 2 : 1

EQUOL CONCENTRATION INCREASING AGENT CONTAINING PSICOSE AS ACTIVE INGREDIENT

TECHNICAL FIELD

The present invention relates to an equol level regulator including psicose as an effective ingredient. Specifically, the present invention relates to an equol level regulator including psicose as an effective ingredient to accelerate the production of equol by human intestinal fauna.

BACKGROUND ART

Equol is an isoflavan compound having a structure represented by Formula 1, and is produced through conversion of isoflavonoids in foods by intestinal fauna in response to consumption of beans.

[Formula 1]

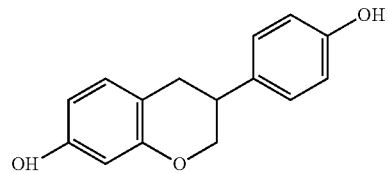

It is reported that equol, which is an active metabolite of soybean isoflavone, has the key role in the efficacy of soybean foods in clinical applications. Namely, much research have shown that equol, which is a metabolite of soybean isoflavone, is more effective to breast cancer, prostate cancer, anti-aging, menopausal disorder and postmenopausal osteoporosis than soybean isoflavone (See. [D. Ingram, et al., (1997) Lancet, 350, 990-994]; [A. M. Duncan, et al., (2000) Cancer Epidemiology, Biomarkers & Prevention, 9, 581-586]; [C. Atkinson, et al., (2002) J. Nutr., 32(3), 595S]; [H. Akaza, et al., (2002) Jpn. J. Clin. Oncol., 32(8), 296-300]; [S. Uchiyama, et al., (2001) Ann Nutr. Metab., 45, 113(abs); Biol Reprod. 2004; 70: 1188-95], and the like).

It is also reported that equol is produced by intestinal bacteria, and the production of equol differs depending on the ability of an individual to produce equol [see: Nutr Cancer. 2000; 36:27-32]. It is estimated that a person who is unable to produce equol does not have bacteria capable of producing equol in the intestine. In such a case, it is thought that such a person cannot expect desired anti-estrogen effects or estrogen-like effects even if soybean processed foods are consumed by the person. In order to achieve desired effects, a person may intake live bacteria capable of producing equol or equol itself.

On the other hand, although production of such a useful equol can be attempted through bioengineering synthesis, there are some technical problems to be overcome due to the fact that the production of equol consists of complex biochemical pathways requiring various microorganisms (see FIG. 2), and that equol-producing microorganisms have very slow growth and reaction rates, like most anaerobic microorganisms.

Accordingly, for the purpose of more practical research, many studies have focused on the investigation of intestinal bacteria capable of producing equol or materials capable of promoting equol production. *Bacteroides ovatus*, *Streptococcus intermedius*, and *Streptococcus constellatus* are reported as microorganisms having equol production capability (International Patent Application Publication 1999/07392). Furthermore, through various prior investigations, it has been reported that various monosaccharides or polysaccharides have excellent ability to increase or decrease equol concentration. Specifically, saccharides such as adonitol, arabinose, erythritol, galactose, lactitol, melezitose, trehalose, ribose, sorbose, xylose, inositol and solbitol and the like contribute to increased equol concentration (see: Table 1 below in International Patent Application Publication 2007/052749).

TABLE 1

| Saccharide | Equol concentration in medium (µM) | Activity to regulate equol concentration (%) |
|---|---|---|
| Adonitol | 47.0 | 260.0 |
| Arabinose | 70.6 | 391.1 |
| Cellobiose | 29.0 | 160.6 |
| Erythritol | 38.7 | 214.2 |
| Fructo-oligo saccharides | 0.0 | 0.0 |
| Fructose | 9.3 | 51.5 |
| Galactose | 65.0 | 240.1 |
| Glucose | 0.0 | 0.0 |
| Glycogen | 33.4 | 184.8 |
| Inulin | 0.0 | 0.0 |
| Lactitol | 82.9 | 459.1 |
| Lactose | 0.0 | 0.0 |
| Lactulose | 1.5 | 8.1 |
| Inositol | 75.2 | 416.2 |
| Maltose | 10.6 | 58.5 |
| Mannitol | 32.9 | 182.2 |
| Mannose | 15.0 | 83.0 |
| Melezitose | 74.3 | 411.6 |
| Melibiose | 4.5 | 24.8 |
| Raffinose | 0.0 | 0.0 |
| Rhamnose | 21.0 | 116.4 |
| Ribose | 59.5 | 329.6 |
| Sorbiol | 67.3 | 372.5 |
| Sorbose | 84.5 | 467.7 |
| Sucrose | 0.0 | 0.0 |
| Galacto-oligosaccharides | 0.0 | 0.0 |
| Trehalose | 72.9 | 403.5 |
| Xylose | 79.9 | 442.6 |
| Saccharide no add | 18.1 | 100.0 |

Psicose is a monosaccharide having sweetness similar to that of sugar and ultra low calories, and thus is widely used as a functional sweetener. Specifically, psicose is classified as a keto-hexose, which is a rare sugar found in trace amounts in nature. It has been reported that psicose is produced from fructose by D-tagatose 3-epimerase. The intensity and sweetness of psicose are very similar to those of fructose. However, unlike fructose, because psicose is almost not metabolized when psicose is consumed in the body, psicose has almost zero-calories, and inhibits enzyme activity relating to lipid synthesis, thereby reducing abdominal obesity. In this regard, psicose may be used as an effective ingredient for diet foods. Furthermore, sugar alcohols, which are widely used as sugar substitutes, have side effects such as diarrhea when consumed in certain amounts, while psicose has substantially no side effects (see Matsue, T., Y. Baba, M. Hashiguchi, K. Takeshita, K. Izumori, and H. Suzuki. 2001. Dietary D-psicose, a C-3 epimer of D-fructose, suppresses the activity of hepatic lipogenic enzymes in rats. Asia Pac. J. Clin. Nutr. 10:233-237; Matsuo, T., and K. Izumori. 2004. D-psicose, a rare sugar that provides no energy and additionally beneficial effects for clinical nutrition. Asia Pac. J. Clin. Nutr. 13:S127).

The present inventors set out to investigate functional foods having a capability to accelerate equol conversion, besides general sugars and polysaccharides reported until now. As a result of continuous efforts, it has been found that psicose known as a functional sweetener exceptionally promotes the production of equol. Based on the results, the present invention has been accomplished.

In order to evaluate relative comparison of equol conversion efficacy of various saccharides, materials showing high conversion promoting rate were primarily selected based on the literature. Representative materials having excellent equol conversion promoting rate selected based on the literature may include lactitol, inositol, melezitose, sorbose, trehalose, and xylose.

Further, the present inventors focused on general, naturally occurring saccharides rather than sugar alcohols, and selected xylose as a representative comparison material. In order to minimize difference in experimental method and incorrectness on experimental errors, the present inventors defined saccharides exhibiting relatively high conversion rate than xylose as test materials having an effect of promoting equol conversion rate. The present inventors performed a series of experiments on novel general (functional) saccharides, which did not satisfy the purpose, and obtained a significant result that psicose promotes equol production. Based on such results, the present invention has been accomplished.

The present invention relates to an equol level regulator including psicose as an effective ingredient. More specifically, the present invention relates to an equol level regulator including psicose as an effective ingredient to accelerate equol production by human intestinal fauna.

DISCLOSURE

Technical Problem

The present invention is aimed at providing a functional food that effectively promotes equol production, besides general saccharides and polysaccharides reported until now.

In addition, the present invention is aimed at providing a novel use of psicose.

Further, the present invention is aimed at providing a composition or food which is free from side effects and is physiologically active and capability to accelerate equol conversion when consumed in the human body.

Technical Solution

As a result of continuous endeavors to solve the technical problem, the present inventors have found that psicose, a functional sweetener, which is safe as food and has low calories, may increase equol concentration. Based on this finding, the present inventors accomplished the present invention.

Further, the present inventors have also found that use of media containing psicose preferentially promotes growth of microorganisms having equol conversion capability or promotes equol conversion.

Advantageous Effects

The present invention provides a composition or food which is free from side effects and is physiologically active and promotes equol conversion when consumed by a person.

MODE FOR INVENTION

Figure 1:
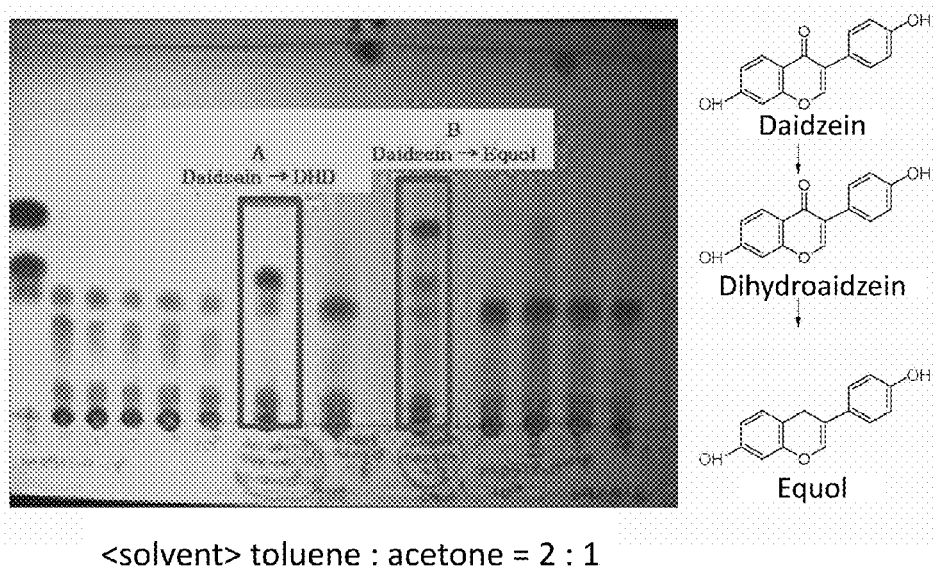
FIG. 1 shows thin layer chromatography using toluene: acetone=2:1 as a developing solvent, illustrating the production of equol from daidzein and dihydrodaidzein (DHD), wherein Dz represents daidzein and DHD represents dihydrodaidzein. An equol producing microorganism population produced equol using daidzein till three days. After three days, all of DHD was converted to equol.
Figure 2:
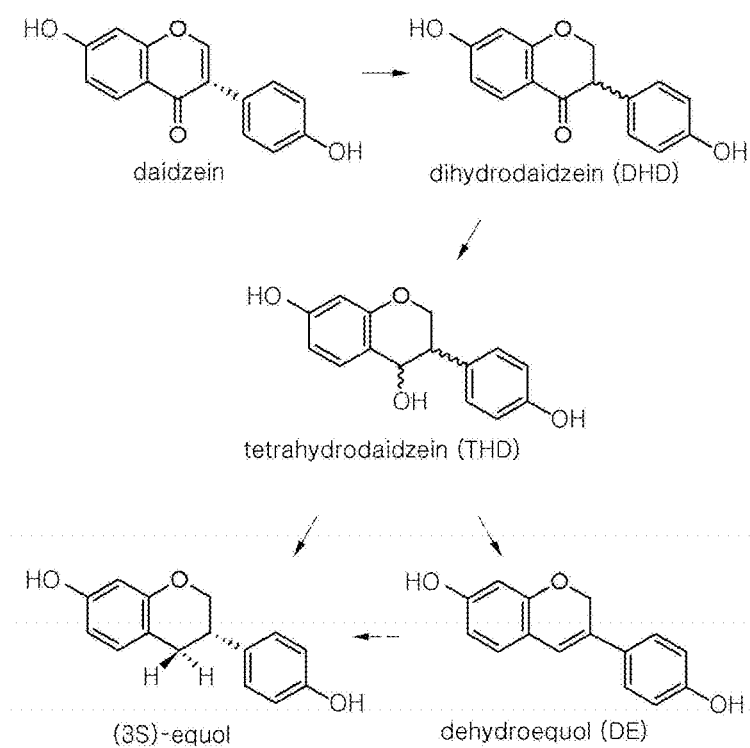
FIG. 2 shows a metabolic pathway of daidzein in intestinal fauna known in the art.
Figure 3:
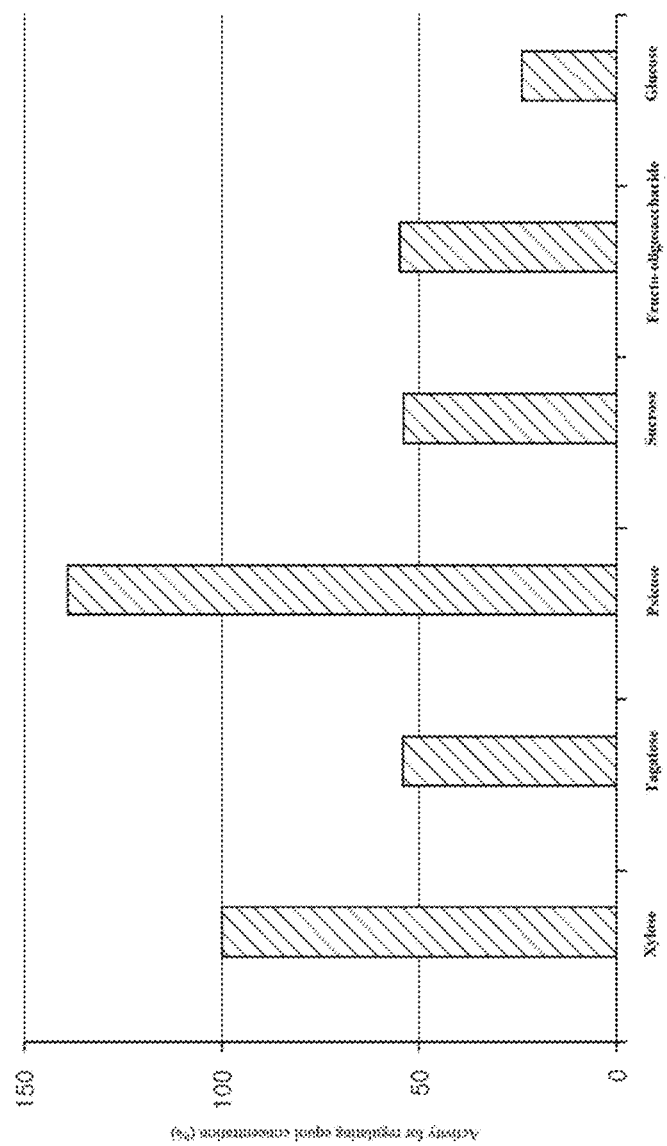
FIG. 3 is a graph depicting effects of various saccharides on equol conversion.

Psicose used herein refers to D-psicose. D-psicose is contained in molasses or isomerized glucose syrup in a trace amount, and is a sort of rare sugars capable of being produced enzymatically from D-fructose by epimerase. D-psicose is expected to have physiological functions such as antioxidative activity, has substantially zero-calories, and provides excellent solubility regardless of sweetness equivalent to about 60% to 70% that of sugar.

One embodiment of the present invention relates to an equol level regulator including psicose as an effective ingredient. The effect of increasing equol concentration of psicose may be caused by selectively multiplying microorganisms having equol conversion capability or promoting the equol conversion capability.

Psicose having an equol concentration increasing function may be utilized as an equol level regulator in the body, blood and intestines such as colon. The equol level regulator including this saccharide as an effective ingredient may be employed to treat, ameliorate, or prevent various diseases associated with isoflavones, such as menopausal disorder including general malaise and the like, osteoporosis, hyperlipidemia, atherosclerosis, breast cancer, prostate cancer, premenstrual syndrome, and the like.

As conventional methods for preparing equol, methods for fermenting materials including daidzein with a microorganism (hereinafter referred to as "equol producing microorganism"), which metabolizes daidzein into equol, are known. Accordingly, psicose according to the present invention is preferably used with daidzein as a substrate for equol. As daidzein, commercially available products such as synthesized products or natural extracts and the like may be utilized, or natural substances containing much daidzein or processed products thereof may also be utilized. Specifically, examples of substances containing much daidzein may include soybeans, peas, kudzu, clovers, and the like. Examples of processed products of substances containing much daidzein may include tofu, soybean milk, fried foods, natto, soy sauce, soybean paste, tempeh, and the like. Further, since isoflavone glycosides are generally aglyconized by intestinal bacteria in the body, daidzein may be utilized in the form of daidzin, malonyldaidzin, acetyldaidzin, and the like which are glycosides of daidzein.

In the present invention, known equol producing strains may be used without specific limitation. Examples of equol producing strains may include *Bacteroides ovatus*, *Streptococcus intermedius*, *Streptococcus constellatus*, *Lactococcus garvieae*, and the like. More specifically, mention may be made *Bacteroides* E-23-15(FERM BP-6435), *Streptococcus* E-23-17(FERM BP-6436), *Streptococcus* A6G225 (FERM BP-6437), *Lactococcus* 20-92(FERM BP-10036), and the like.

According to the present invention, psicose may be added to a medium for the conventional method for producing equol to allow fermentation of equol producing microorganisms, thereby increasing equol concentration.

In this embodiment, the equol level regulator according to the present invention may further include other saccharides known to increase equol concentration. Examples of other saccharides to be further added may include adonitol, arabinose, erythritol, galactose, lactitol, melezitose, trehalose, ribose, sorbose, xylose, inositol or sorbitol and the like, without being limited thereto.

Therefore, another embodiment of the present invention relates to a method for increasing equol concentration including adding psicose to a culture medium for equol producing microorganisms.

A further embodiment of the present invention provides a culture medium containing psicose for equol producing strain.

Yet further embodiment of the present invention relates to a food including psicose for increasing equol concentration.

In one embodiment of the invention, difference in amount of produced equol depending upon sorts of carbohydrates was investigated using a microorganism population, which is an aggregate of various intestinal fauna. As a result, it was confirmed that carbohydrates exert influences on changes in microflora or growth of equol producing microorganisms (Example 2). Specifically, unlike the case where pure daidzein was used, the reaction rate of producing equol was changed when carbohydrates were added. Namely, the production of equol was performed more slowly for a long period of time.

It was found that psicose significantly promoted equol production under the reaction condition for three days (Example 2).

The activity for regulating equol concentration by psicose was calculated as follows. To a microorganism population stock having capability to produce equol (obtained by centrifuging and washing feces taken from equol producers, KR Patent Registration No. 2008-0072635), daidzein as a substrate for equol, and psicose were added, followed by culturing and measuring the equol concentration in a culture solution. The measured equol concentration was inserted together with equol concentration in a culture solution containing daidzein and xylose into Equation for calculating equol variation percentage below:

Equol variation percentage (%)=(Equol concentration in the culture solution containing psicose and daidzein)/(Equol concentration in the culture solution containing xylose and daidzein)×100

The dose of equol level regulator according to the present invention is not particularly limited. Since the effect of the equol level regulator varies depending upon use aspects such as subjects or diseases to be treated, and the like, it is necessary to determine a suitable dose. The equol level regulator is preferably added in an amount of 0.1 mg to 100 g per day, specifically 50 mg to 50 g per day.

The equol level regulator may be administered by orally or parenterally. Oral administration is preferred. In administration, psicose as an effective ingredient is mixed with a solid or liquid nontoxic carrier for medicines suitable for administration methods, such as oral administration, rectal administration, injection and the like, followed by administration in a conventional medicine formulation type.

Examples of such formulations may include solid formulations, such as tablets, granules, powders, capsules, and the like, liquid formulations, such as solutions, suspensions, emulsions, and the like, lyophilizing agents, and the like. These formulations may be prepared by a conventional method. Examples of nontoxic carriers for medicines may include starch, dextrin, fatty acid glycerides, polyethylene glycols, hydroxyethylene starches, ethylene glycol, polyoxyethylene sorbitan fatty acid esters, amino acids, gelatin, albumin, water, saline solution, and the like. In addition, general additives such as stabilizers, wetting agents, emulsifying agents, binders, isotonic agents, excipients, and the like may be optionally added, as necessary.

Further, the saccharide according to the present invention may be used not only as medicine formulations, but also as food. In this case, the saccharide according to the present invention may be used per se, or may be used in food together with various nutrients. In the case of using psicose capable of increasing equol concentration, it may be used to increase equol concentration in the body, or may be used as food for health or food substances useful for ameliorating and preventing menopausal disorder including general malaise and the like, osteoporosis, hyperlipidemia, atherosclerosis, breast cancer, prostate cancer, premenstrual syndrome, and the like.

Specifically, when the saccharide according to the present invention is added to food, the saccharide may be provided in edible form by appropriately employing food additives through conventional means, namely, granules, particles, tablets, capsules, paste, and the like. Alternatively, the saccharide may be added to various foods, for example, processed meats such as ham, sausages, and the like, processed seafood such as fish paste, boiled fish paste, and the like, bread, cookies, butter, powder milk, fermented milk products, or drinks such as water, fruit juice, milk, soft drinks, tea drinks, and the like. Foods may include animal feeds.

Conventional equol producing strains are known to use, as a substrate, dihydrodaidzein (DHD) only, which is a reduction product of daidzein. Since a microorganism population stock contains various microorganisms, reaction from daidzein to DHD may be performed. In this regard, the production of equol was analyzed by TLC using microorganism population capable of producing equol using both daidzein and DHD as substrates. The change in equol production amount in the presence of carbohydrates was measured.

Example 1

Activation of Equol Producing Microorganism Population and Measurement of Equol Production in Standard Condition 1) Measurement of Equol Production GAM (Gifu anaerobic medium) medium (4 ml) was inoculated with equol producing microorganism population stock stored in liquid nitrogen (obtained by centrifuging and washing feces taken from equol producers, KR Patent Registration No. 2008-0072635), followed by cultivating for 3~4 hours to activate.

When OD (optical density) approached 1.5, 200 μl of medium was taken and transferred to an Eppendorf tube. To the Eppendorf tube, 0.1 mM of daidzein was added, followed by vortexing to initiate reaction.

In order to measure equol production over time, 50 μl of medium was sampled 1, 2 and 3 days after the inoculation.

To the medium, 1 ml of ethyl acetate was added to extract isoflavonoids. Extraction was performed as follows: after vortexing and centrifugation, 800 μl of ethyl acetate was taken from the medium, followed by removal of the solvent through vacuum drying. Then, the resultant was dissolved in 10 μl of methanol. 2 μl was used to perform TLC.

1) Result

From TLC, it was found that the microorganism population produced equol from daidzein, and the amount of produced equol continuously increased for three days after inoculation. After three days, daidzein provided as a substrate was not detected. The microorganism conversion experiment was carried out for three days.

Example 2

Chance in Produced Equol Amount in the Presence of Carbohydrate

Variation in produced equol amount was measured using six carbohydrates, namely, xylose, tagatose, psicose, sucrose, fructo-oligosaccharide, and glucose, under the same equol production conditions as in Example 1.

1) Microorganism Reaction and Comparison of Produced Equol Amount

Equol producing microorganism population was inoculated and the product was extracted in the same manner as in Example 1 except that, before the substrate was inoculated with the activated microorganism population, the final concentration of carbohydrate was adjusted to 1% by adding 2 mg each of xylose, tagatose, psicose, sucrose, fructo-oligosaccharide, and glucose. Further, only daidzein was used as the substrate. Unlike the case where pure daidzein was used, the reaction rate of producing equol was changed when carbohydrates were added. Namely, the production of equol occurred more slowly for a long period of time.

In order to compare variation in the produced equol amount in the product, quantitative analysis of TLC results was performed using an image analyzer.

2) Result

Assuming the produced equol amount in the culture solution containing xylose and daidzein to be 100, the produced equol amount after addition of each carbohydrate for three days was compared. The comparison results are as follows. (Table 2 shows comparison results between the produced equol amount depending upon each sort of carbohydrate and the produced equol amount in the culture solution containing xylose and daidzein. The results are average values of image analysis results for two coloring methods.)

TABLE 2

| Carbohydrate | Xylose | Tagatose | Psicose | Sucrose | Fructo-oligosaccharide | Glucose |
|---|---|---|---|---|---|---|
| Variation (%) | 100 | 54 | 139 | 54 | 55 | 24 |

Example 3

Equol Level Regulator in Tablet Form

Various components listed below were mixed, granulated and dried, and supplied to a tablet press to form tablets.

| | |
|---|---|
| Microcrystalline cellulose | 110 mg |
| Psicose | 75 mg |
| Magnesium stearate | 0.4 mg |
| Methylcellulose | 13 mg |

Example 4

Equol Level Regulator in Soft Drink Form

Various components listed below were mixed and homogenized to prepare a soft drink.

| | |
|---|---|
| Fragrance | 0.7 g |
| Psicose | 2.0 g |
| Citric acid | 0.4 g |
| Fructose | 5 g |
| Distilled water | 80 g |

The invention claimed is:

1. A method for producing equol, comprising:
adding psicose to a culture medium, wherein the culture medium comprises diadzein as a substrate for producing equol, and
culturing an equol-producing microorganism in the culture medium, thereby producing equol.

2. The method according to claim 1, wherein the equol-producing microorganism is *Bacteroides ovatus, Streptococcus intermedius, Streptococcus constellatus*, or *Lactococcus garvieae*.

* * * * *